(12) United States Patent
Kan et al.

(10) Patent No.: US 12,220,483 B2
(45) Date of Patent: Feb. 11, 2025

(54) LIPOSOME COMPOSITIONS COMPRISING WEAK ACID DRUGS AND USES THEREOF

(71) Applicant: Pharmosa Biopharm Inc., Taipei (TW)

(72) Inventors: Pei Kan, Taipei (TW); Yi Fong Lin, New Taipei (TW); Ko Chieh Chen, Taipei (TW)

(73) Assignee: Pharmosa Biopharm Inc., Taipei (TW)

( * ) Notice: Subject to any disclaimer, the term of this patent is extended or adjusted under 35 U.S.C. 154(b) by 0 days.

(21) Appl. No.: 18/608,182

(22) Filed: Mar. 18, 2024

(65) Prior Publication Data

US 2024/0216277 A1 Jul. 4, 2024

Related U.S. Application Data

(63) Continuation of application No. 16/043,126, filed on Jul. 23, 2018, now Pat. No. 11,964,050.

(60) Provisional application No. 62/595,207, filed on Dec. 6, 2017, provisional application No. 62/536,034, filed on Jul. 24, 2017.

(51) Int. Cl.
*A61K 9/127* (2006.01)
*A61K 31/5585* (2006.01)
*A61K 47/02* (2006.01)
*A61P 11/06* (2006.01)

(52) U.S. Cl.
CPC ............ *A61K 9/127* (2013.01); *A61K 9/1271* (2013.01); *A61K 9/1278* (2013.01); *A61K 31/5585* (2013.01); *A61K 47/02* (2013.01); *A61P 11/06* (2018.01)

(58) Field of Classification Search
CPC ...................................................... A61K 9/127
See application file for complete search history.

(56) References Cited

U.S. PATENT DOCUMENTS

| | | | |
|---|---|---|---|
| 4,906,476 A * | 3/1990 | Radhakrishnan | A61K 9/1277 424/450 |
| 5,088,499 A | 2/1992 | Unger | |
| 5,149,319 A | 9/1992 | Unger | |
| 5,192,549 A | 3/1993 | Barenolz et al. | |
| 5,262,168 A | 11/1993 | Lenk et al. | |
| 5,616,341 A | 4/1997 | Mayer et al. | |
| 5,811,118 A | 9/1998 | Ostro et al. | |
| 5,939,096 A | 8/1999 | Clerc et al. | |
| 5,972,379 A | 10/1999 | Guo et al. | |
| 8,318,198 B1 | 11/2012 | Sung et al. | |
| 8,318,200 B1 | 11/2012 | Sung et al. | |
| 2006/0159736 A1 | 7/2006 | Zalipsky et al. | |
| 2011/0104052 A1 | 5/2011 | Barnett et al. | |
| 2013/0052259 A1 | 2/2013 | Barenholz et al. | |
| 2014/0328897 A1 | 11/2014 | Jolck et al. | |
| 2014/0328899 A1 | 11/2014 | Gabizon et al. | |
| 2015/0093434 A1 | 4/2015 | Barenholz et al. | |
| 2015/0328232 A1 | 11/2015 | Malinin et al. | |
| 2019/0022004 A1 | 1/2019 | Kan et al. | |

FOREIGN PATENT DOCUMENTS

| | | | |
|---|---|---|---|
| CA | 2 714 512 | * | 8/2009 |
| CN | 104984367 A | | 10/2015 |
| EP | 0361894 A1 | | 4/1992 |
| EP | 0 512 916 | * | 11/1992 |
| JP | H02196713 A | | 8/1990 |
| JP | H10130169 A | | 5/1998 |
| JP | 2009513621 A | | 4/2009 |
| WO | 9300888 A1 | | 1/1993 |
| WO | 9614257 A1 | | 5/1996 |
| WO | 9625147 A1 | | 8/1996 |
| WO | 2007049278 A2 | | 5/2007 |
| WO | 2007049279 A2 | | 5/2007 |
| WO | 2007107304 A2 | | 9/2007 |
| WO | 2018031568 A1 | | 2/2018 |

OTHER PUBLICATIONS

Rahul Nahire et al., "pH-Triggered Echogenicity and Contents Release from Liposomes," Molecular Pharmaceutics, Oct. 1, 2014, pp. 4,059-4,068, vol. 11, No. 11.
Andreas Fritze et al., "Remote loading of doxorubicin into liposomes driven by a transmembrane phosphate gradient," Biochimica et Biophysica Acta, Jun. 14, 2006, pp. 1,633-1,640, vol. 1,758, No. 10.
Ko-Jie Chen et al., "A thermoresponsive bubble-generating liposomal system for triggering localized extracellular drug delivery," ACS Nano, Dec. 14, 2012, pp. 438,446, vol. 7, No. 1.
Min-Fan Chung et al., "A Liposomal System Capable of Generating $CO_2$ Bubbles to Induce Transient Cavitation, Lysosomal Rupturing, and Cell Necrosis," Angew. Chem. Int. Ed., Sep. 5, 2012, pp. 10,089-10,093, vol. 51.
Yuval Avnir et al., "Fabrication principles and their contribution to the superior in vivo therapeutic efficacy of nano-liposomes remote loaded with glucocorticoids," PLoS One, Oct. 2011, vol. 6, No. 10, e25721.
International Search Report and Written Opinion for PCT/US2018/043221, mailed Oct. 12, 2018.
Kazufumi Nakamura, et al., "Advancement of Basic Research in Pulmonary Arterial Hypertension", Latest Medicine, (2017) vol. 72, No. 8, p. 49-53.
Office action for related Japanese application No. 2020-503870, JP Nat'l Stage date Jul. 23, 2018, mailed Mar. 9, 2021.
Extended European Search Report for corresponding EP Application No. 18838053.9, mailed Apr. 6, 2021.
Office action for related Russa application No. 2020102279, mailed Sep. 23, 2021.
Office Action for China Application No. 201880049079.3, mailed Sep. 14, 2022.
Office Action for China Application No. 201880049079.3, mailed Apr. 12, 2023.
Supplementary Action for China Application No. 201880049079.3.
Office Action for BR Application BR112020001411-7, mailed Jun. 22, 2022.

(Continued)

*Primary Examiner* — Benjamin J Packard
(74) *Attorney, Agent, or Firm* — Piloff Passino & Cosenza LLP; Rachel K. Piloff; Sean A. Passino

(57) ABSTRACT

The present invention relates to a pharmaceutical composition comprising a weak acid drug, with the use of a bicarbonate salt to achieve a high incorporation of the drug into the liposome and a better therapeutic efficacy. Also disclosed is a method for treating a respiratory disease using the pharmaceutical composition disclosed herein.

20 Claims, No Drawings

(56) References Cited

OTHER PUBLICATIONS

Office Action for TW application 107125393, mailed Sep. 26, 2020.
Office Action for AU application 2018307509, mailed Nov. 26, 2020.
Office Action for CA application 3,070,951, mailed Apr. 21, 2021.
Office Action for CA application 3,070,951, mailed Nov. 17, 2021.
Office Action for Israel application 272187, mailed Dec. 15, 2021.
Office Action for India application 202017002812, mailed Aug. 2, 2020.
Office Action for Indonesia application P00202000652, mailed Jul. 23, 2021.
Office Action for Korea application 10 2020 7001608, mailed Mar. 19, 2021.
Office Action for Mexico application MX/a/2020/000857, mailed May 17, 2022.
Office Action for Mexico application MX/a/2020/000857, mailed Aug. 25, 2022.
Office Action for Russia application 2020102279, mailed Feb. 16, 2022.
Office Action for Saudi Arabia application 520411119, mailed Dec. 15, 2021.
Office Action for Saudi Arabia application 520411119, mailed Jan. 29, 2023.

* cited by examiner

LIPOSOME COMPOSITIONS COMPRISING WEAK ACID DRUGS AND USES THEREOF

CROSS-REFERENCE TO RELATED APPLICATIONS

This application is a Continuation of U.S. patent application Ser. No. 16/043,126, filed 23 Jul. 2018, which claims the benefit of U.S. application Ser. No. 62/536,034, filed on 24 Jul. 2017 and U.S. application Ser. No. 62/595,207, filed on 6 Dec. 2017, the entire disclosures of each of which are incorporated herein by reference.

TECHNOLOGY FIELD

The present invention relates to a pharmaceutical composition with high drug encapsulation efficiency or loading, methods of making and the uses of the pharmaceutical composition disclosed herein.

BACKGROUND OF THE INVENTION

Liposomes are vesicles formed by lipid bilayers containing an internal aqueous medium. Liposomes have been used as carriers for a variety of therapeutic agents to offer improved delivery properties, such as enhanced blood circulation time, reduced cytotoxicity, sustained drug release, and specific drug delivery to selected tissues. When using liposomes for therapeutic drug delivery, a higher drug encapsulation efficiency is desirable.

Currently, a number of drug-loading methods are available for incorporating drugs into liposomes. For weak acid drugs, liposomes having a higher inside/lower outside pH gradient has been reported for drug loading, for example, in U.S. Pat. No. 5,939,096. The pH gradient is established by a salt of a weak acid, including carboxylic acid such as formic acid, acetic acid, propanoic acid, butanoic acid, pentanoic acid, and substituted derivatives thereof. WO 96/25147 discloses the use of a bicarbonate salt for drug loading. However, later researches suggest that the use of a bicarbonate salt in liposome preparation causes gas accumulation that would disrupt and destabilize the liposomes and trigger premature drug release (Nahire et al. pH-triggered echogenicity and contents release from liposomes, Mol Pharm. 2014 Nov 3;11(11):4059-68; and Chen et al. A thermoresponsive bubble-generating liposomal system for triggering Localized Extracellular Drug Delivery, ACS Nano. 2013 Jan 22;7(1):438-46), which suggest bicarbonate salt should be avoided as a loading agent due to its disruptive and destabilizing effect on the liposomes.

Many problems still remain unsolved in relation to weak acid drugs using conventional liposomes, including poor drug loading and unsatisfactory controlled release rate. There is still an unmet need for liposome suspensions with a high drug loading efficiency to increase therapeutic efficacy. The present invention addresses this need and other needs.

BRIEF SUMMARY OF THE INVENTION

In one embodiment, the present invention discloses a pharmaceutical composition comprising one or more liposomes, comprising (a) a lipid bilayer, comprising at least one vesicle-forming lipid; and (b) an internal aqueous medium inside the lipid bilayer comprising a bicarbonate salt and a weak acid drug, wherein the liposomes are suspended in an external medium and the molar ratio of the drug to the bicarbonate salt is from about 0.1:1 to 1:1.

Another embodiment of the present invention provides for a pharmaceutical composition comprising one or more liposomes, comprising (a) a lipid bilayer, comprising at least one vesicle-forming lipid; and (b) an internal aqueous medium inside the lipid bilayer comprising a bicarbonate salt and a weak acid drug, wherein the liposomes are suspended in an external medium and the concentration of the bicarbonate salt is about 50 mM to less than about 1000 mM.

A third embodiment of the present invention provides for a pharmaceutical composition, comprising one or more liposomes, comprising (a) a lipid bilayer, comprising at least one vesicle-forming lipid; and (b) an internal aqueous medium inside the lipid bilayer comprising a bicarbonate salt and a weak acid drug, wherein the liposomes are suspended in an external medium and the pH of the external medium is above the $pK_a$ of the weak acid drug.

A fourth embodiment of the present invention provides for a pharmaceutical composition, comprising one or more liposomes, comprising (a) a lipid bilayer, comprising at least one vesicle-forming lipid; and (b) an internal aqueous medium inside the lipid bilayer comprising a bicarbonate salt and prostacyclin, wherein the liposomes are suspended in an external medium and the molar ratio of the prostacyclin and the bicarbonate salt is about 0.1:1 to about 1:1.

A fifth embodiment of the present invention provides for a pharmaceutical composition, comprising one or more liposomes, comprising (a) a lipid bilayer, comprising at least one vesicle-forming lipid; and (b) an internal aqueous medium inside the lipid bilayer comprising a bicarbonate salt and prostacyclin, wherein the liposomes are suspended in an external medium and the concentration of the bicarbonate salt is about 50 mM to less than about 1000 mM.

In yet another embodiment, a pharmaceutical composition comprising one or more liposomes, said liposome comprising (a) a lipid bilayer, comprising at least one vesicle-forming lipid; and (b) an internal aqueous medium inside the lipid bilayer comprising a bicarbonate salt and prostacyclin, wherein the pH of the external medium is above the $pK_a$ of prostacyclin is provided.

The present invention further provides a method for preparing the pharmaceutical composition disclosed herein, comprising the steps of:
(i) preparing a lipid solution using at least one vesicle-forming lipid;
(ii) mixing the lipid solution from step (i) with a bicarbonate salt to form at least one liposome comprising a lipid bilayer and an internal aqueous medium, wherein the liposome is suspended in an external medium;
(iii) adjusting the concentration of the bicarbonate salt in the external medium to produce a lower pH in the external medium of the liposome and a higher pH in the internal aqueous medium of the liposome, wherein the pH of the external medium is above the $pK_a$ of a weak acid drug; and
(iv) adding the weak acid drug to the external medium.

Also provided are methods for treating a respiratory disease, comprising the steps of administering the pharmaceutical composition disclosed herein to a subject in need thereof.

The invention also provides the pharmaceutical composition disclosed herein for its use in the treatment and/or prophylactic treatment of respiratory disease.

The invention also includes the use of the pharmaceutical composition disclosed herein for the manufacture of a medicament for the therapeutic and/or prophylactic treatment of respiratory disease.

The details of one or more embodiments of the invention are set forth in the description below. Other features or advantages of the present invention will be apparent from the following detailed description of several embodiments, and also from the appending claims. Statements containing these terms should be understood not to limit the subject matter described herein or to limit the meaning or scope of the patent claims below. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification, any or all drawings and each claim.

DETAILED DESCRIPTION OF THE INVENTION

Unless defined otherwise, all technical and scientific terms used herein have the same meanings as is commonly understood by one of skill in the art to which this invention belongs.

As used herein, the articles "a" and "an" refer to one or more than one (i.e., at least one) of the grammatical object of the article. By way of example, "an element" means one element or more than one element.

The term "comprise" or "comprising" is generally used in the sense of include/including which means permitting the presence of one or more features, ingredients or components. The term "comprise" or "comprising" encompasses the term "consists" or "consisting of."

All numbers are modified by the term "about". As used herein, the term "about" refers to a range of ±10% of a specified value.

The term "subject" can refer to a vertebrate having a respiratory disease or to a vertebrate deemed to be in need of treatment for a respiratory disease. Subjects include warm-blooded animals, such as mammals, such as a primate, and, more preferably, a human. Non-human primates are subjects as well. The term subject includes domesticated animals, such as cats, dogs, etc., livestock (for example, cattle, horses, pigs, sheep, goats, etc.) and laboratory animals (for example, mouse, rabbit, rat, gerbil, guinea pig, etc.). Thus, veterinary uses and medical formulations are contemplated herein.

As used herein, "substantially free" means that pharmaceutical composition contains less than 5%, 4%, 3%, 2% or 1% of a specific substance. In some embodiments, pharmaceutical composition does not contain the specific substance.

The term "liposome" as used herein refers to microscopic vesicles or particles made up of one or more lipid bilayers enclosing an internal aqueous medium. To form liposomes, the presence of at least one "vesicle-forming lipid" is needed, which is an amphipathic lipid capable of either forming or being incorporated into a lipid bilayer. Any suitable vesicle-forming lipid may be used to form the lipid bilayer constituting the liposomes. Vesicle-forming lipid includes, but not limited to, phospholipids such as phosphatidylcholine (PC), phosphatidylglycerol (PG), phosphatidylinositol (PI), phosphatidic acid (PA), phosphatidyethanolamine (PE) or phosphatidylserine (PS), and charged lipids, such as a positively charge lipid or a negatively charged lipid.

The lipid bilayer of the liposome includes at least one vesicle-forming lipid and a sterol, which is selected from the group consisting of cholesterol, cholesterol hexasuccinate, ergosterol, lanosterol, and any combination thereof, but is not limited thereto. In an exemplary embodiment, the sterol is cholesterol.

In some embodiments, the vesicle-forming lipid is a mixture of a fist phospholipid and a second phospholipid. In certain embodiments, the first phospholipid is phosphatidylcholine (PC), which is selected from the group consisting of hydrogenated egg phosphatidylcholine (HEPC), hydrogenated soy phosphatidylcholine (HSPC), dipalmitoyl phosphatidylcholine (DPPC), distearyloyl phosphatidylcholine (DSPC), diarachidoyl phosphatidylcholine, dimyristoyl phosphatidylcholine (DMPC), egg phosphatidylcholine (EPC), soy phosphatidylcholine (SPC), oleoyl palmitoyl phosphatidylcholine, dioleoyl phosphatidylcholine (DOPC), dipetroselinoyl phosphatidylcholine, palmitoylelaidoyl phosphatidylcholine, palmitoylolcoyl phosphatidylcholine, dilauroyl phosphatidylcholine (DLPC), diundecanoyl phosphatidylcholine, didecanoyl phosphatidylcholine, dinonanoyl phosphatidylcholine, and any combination thereof. In other embodiments, the second phospholipid is a polyethylene glycol modified phospholipid, containing a polyethylene glycol having a molecular weight of about 500 to about 10,000 daltons, such as 1,2-distearoly-sn-glycero-3-phosphoethanolamine-N-[methoxy(polyethylene glycol)-2000] (DSPE-PEG2000), a negatively charged phospholipid, such as distearyloyl phosphatidylglycerol (DSPG), Dipalmitoylphosphatidylglycerol (DPPG) or dimyristoylphosphatidylglycerol (DMPG) or (DOPG). In an exemplary embodiment, the mole percent of the first phospholipid: cholesterol: the second phospholipid is 50-70: 20-45: 0.1-10, 50-70: 20-45: 0.5-8 or 55-65:25-40:1-6

In other embodiments, the vesicle-forming lipids is a mixture of a first phospholipid and a charged lipid. In an exemplary embodiment, vesicle-forming lipids is a mixture of a first phospholipid, a second phospholipid and a charged lipid. The charged lipid, includes stearylamine, 1,2-diolcoyl-3-trimethylammonium-propane (DOTAP), 3β-[N-(N',N'-dimethylaminocthane)-carbamoyl]cholesterol (DC-Cholesterol), $N^4$-Cholesteryl-Spermine (GL67), dimethyldioctadecylammonium (DDAB), 1,2-di-O-octadecenyl-3-trimethylammonium propane (DOTMA), ethylphosphocholine (ethyl PC) or combination thereof. In another exemplary embodiment, the mole percent of the first phospholipid: cholesterol: charged lipid is 50-70: 20-45: 0.1-10, 50-70: 20-45: 0.5-8 or 55-65:25-40: 1-6.

In an embodiment, the mole % of HSPC, cholesterol, and DSPG in the lipid bilayer is 50-70: 20-45: 0.1-10, 50-70: 20-45: 0.1-5 or 55-65:25-40:0.5-8. In another embodiment, the mole % of HSPC, cholesterol and DSPE-PEG2000 in the lipid bilayer is 50-70: 20-45: 0.1-10, 50-70: 20-45: 0.1-5 or 55-65:25-40:0.5-8. In another embodiment, the mole % of DPPC:Chol:DSPE-PEG2000 in the lipid bilayer is 50-70: 20-45: 0.5-8, 50-70: 20-45: 0.1-5 or 55-65:25-40:1-6.

In one embodiment, the lipid bilayer of the liposomes may also include at least one vesicle-forming lipid and a surfactant, which can be a non-ionic surfactant, a cationic surfactant or a zwitterionic surfactant. A non-ionic surfactant has no formally charged groups in its head. A cationic surfactant carries a net positive charge in its head. A zwitterion surfactant is electrically neutral but carries formal positive and negative charges on different atoms.

Non limiting examples of non-ionic surfactant include non-ionic water soluble mono-, di-, and tri-glycerides; non-ionic water soluble mono- and di-fatty acid esters of polyethylene glycol; non-ionic water soluble sorbitan fatty acid esters (e.g. sorbitan monooleates such as TWEEN 20 (polyoxyethylene 20 sorbitan monooleate), SPAN 80); non-ionic water soluble triblock copolymers (e.g., poly(ethyleneoxide)/poly-(propyleneoxide)/poly(ethyleneoxide)triblock copolymers such as POLOXAMER 406 (PLURONIC F-127), or derivatives thereof.

Non-limiting examples of cationic surfactant include dimethyldialkylammonium bromide or dodecyltrimethylammonium bromide.

Non limiting examples of zwitterionic surfactant include 3-(N,N-dimethyl palmitylammonio)-propanesulfonate.

In some embodiments, the liposomes is substantially free of an ionophore, which is a compound capable of facilitating the transport of $H^+$ or $OH^-$ across the liposome membrane A solvent for dissolving a vesicle-forming lipid for the preparation of liposomes can be, for example, methanol, ethanol, ether, and combinations thereof. Optionally, the solvent can be removed by a supercritical fluid later, and is preferably used in a minimum amount so as to decrease the time for performing an organic solvent removing step.

According to the present invention, the liposomes are prepared in a medium containing a bicarbonate salt. In particular, when the vesicle-forming lipid is in contact with a medium containing a bicarbonate salt, a liposome suspension is formed.

A "bicarbonate salt" as used herein is preferably a pharmaceutically acceptable salt compound including a bicarbonate anion and a cationic component. In one embodiment, the cationic component of the salt compound is a metal. Non-limiting examples of the metal include a Group IA or IIA metal, such as potassium (K), sodium (Na), calcium (Ca), magnesium (Mg), cesium (Cs), and lithium (Li) or a metal other than Group IA or IIA metal, such as ferrous iron (Fc) and nickel (Ni). Examples of bicarbonate salt include, but not limited to, potassium bicarbonate, sodium bicarbonate, calcium bicarbonate, magnesium bicarbonate, cesium bicarbonate, lithium bicarbonate, nickel bicarbonate, ferrous iron bicarbonate or any combination thereof.

The liposomes in the suspension is subjected to size reduction. A liposome's size is typically referred to its diameter. Liposome size reduction can be accomplished by a number of methods, such as extrusion, sonication, homogenization techniques or milling techniques, which are well known and can be performed by persons skilled in this art. Extrusion includes passing liposomes, under pressure, one or more times through filters having defined pore sizes. The filters are generally made of polycarbonate, but can also be made of any durable material which does not interact with the liposomes and which is sufficiently strong to allow extrusion under sufficient pressure. The size of the liposomes can be reduced by sonication, which employs sonic energy to disrupt or shear liposomes that will spontaneously reform into smaller liposomes. For example, sonication can be conducted by immersing a glass tube containing the liposome suspension into the sonic epicenter produced in a bath-type sonicator, or a probe type sonicator may be used in which the sonic energy is generated by vibration of a titanium probe in direct contact with the liposome suspension. In the present invention, the liposomes generally have a diameter of about 50 nm to 500 nm, such as about 500 nm or less, about 400 nm or less, about 300 nm or less, about 200 nm or less or about 100 nm or less.

After sizing, the concentration of the bicarbonate salt in the external medium is adjusted to provide pH gradient between the internal aqueous medium and the external medium, which can be carried out by a number of ways, for example, by exchanging the external medium with a suitable buffer lacking bicarbonate salts, such as citric acid buffer ($H_3C_6H_5O$) and phosphoric acid buffer ($H_3PO_4$), by methods such as diafiltration, dialysis, ultrafiltration, or tangential flow filtration.

In one embodiment, the bicarbonate salt provides a lower outside and a higher inside pH gradient between the external medium and the internal aqueous medium of the liposomes. In another embodiment, the pH of the internal aqueous medium is at least one unit higher than the pH of the external medium. In yet another embodiment, the pH of the internal aqueous medium is about 7, 8, 9 or 10 and the pH of the external medium is less than 7, less than 6, less than 5, less than 4, less than 3, about 3-7, about 3.5-6.5, or about 4-6. In yet another exemplary embodiment, the pH of the external medium is above the $pK_a$ of the weak acid drug.

The prepared liposome can be stored for substantial periods of time prior to drug loading and administration to a subject. For example, liposomes can be stored at refrigerated conditions for substantial periods of time prior to drug loading. Alternatively, liposomes can be dehydrated, stored, and subsequently rehydrated and loaded with one or more active agents as needed, prior to administration. Liposomes may also be dehydrated after being loaded with one or more weak acid drug. Dehydration can be performed by a number of methods available and known in the art. In some embodiments, liposomes are dehydrated using standard freeze-drying apparatus i.e. dehydration under low pressure conditions. Also, liposomes can be frozen e.g. using liquid nitrogen. Saccharides can be added to the liposomal environment, e.g., to the buffer containing the liposomes, prior to dehydration, to ensure stability and integrity of the liposome during dehydration. Examples of saccharides include but are not limited to maltose, lactose, sucrose, trehalose, dextrose, sorbitol, mannitol, xylitol, or a combination thereof.

A liposome suspension having a lower outside/higher inside pH gradient as described above are ready for drug loading. Typically, a weak acid drug to be loaded is added to the external medium of the liposome and the resultant suspension is incubated under a condition to effect drug loading into the internal aqueous medium of the liposome, allowing diffusion of the weak acid drug into the internal aqueous medium of the liposome and until a desired loading concentration and encapsulation efficiency (the percentage of the internal/encapsulated amount of the drug relative to the total amount of the drug in the composition) is achieved.

A weak acid drug as used herein, unless indicated to the contrary or otherwise evident from the context, also include its pharmaceutically acceptable salt and its protonated form. In one embodiment, a weak acid drug contains at least one functional group selected from the group consisting of a carboxyl group (—COOH), a hydroxyl group (—OH), a phosphate group (—$PO_4$) and any combination thereof. In another embodiment, a weak acid drug has a pKa of less than about 7, less than about 6, between 1 to less than about 7, between 2 to less than about 6, between 2 to 6.9, or between 2.5 to 6. A weak acid drug may also contain one or more functional groups in addition to the above-mentioned carboxyl group (—COOH), hydroxyl group (—OH), and phosphate group (—$PO_4$); such additional functional group(s) should not significantly change the acidity of the drug from that of its non-functionalized counterparts. Table 1 shows the non-limiting examples of the weak acid drug of the present invention.

TABLE 1

Characteristic of weak acid drugs suitable in the present invention

| Functional group | Drug category | Drug species | pKa |
|---|---|---|---|
| COOH | Prostaglandins | Prostaglandin E1 (PGE1) | 4.35 |
| | | Prostaglandin E2 (PGE2) e.g., dinoprostone | 4.3 |
| | | Epoprostenol | 4.43 |
| | | Iloprost | 4.66 |
| | | Beraprost | 4.2 |
| | | MIRE-269 (ACT-333679) | 3.77 |
| | | Prostacycline (treprostinil) | 4.5 |
| | | Ralinepag (APD811) | 3.5 |
| | Glucocorticoids (GCs) | Hydrocortisone sodium succinate | 3.66 |
| | | Methylprednisolone sodium succinate | 4.6 |
| | | Methylprednisolone Hemisuccinate (MPSS) | 4.29 |
| | Salicylates | Aspirin (acetylsalicylic acid) | 3.5 |
| | | Salicylic acid and other salicylates | 2.97 |
| | Propionic acid derivatives | Ibuprofen sodium | 5.2 |
| | | Dexibuprofen | 4.42 |
| | | Naproxen sodium | 4.15 |
| | | Fenoprofen | 4.5 |
| | | Ketoprofen sodium | 4.76 |
| | | Dexketoprofen | 5.9 |
| | | Flurbiprofen | 4.3 |
| | | Oxaprozin | 4.95 |
| | | Loxoprofen | 4.2 |
| | Acetic acid derivatives | Indomethacin sodium | 4.5 |
| | | Tolmetin | 3.5 |
| | | Etodolac | 4.7 |
| | | Ketorolac sodium | 3.8 |
| | | Diclofenac sodium | 4.2 |
| | | Aceclofenac | 4.7 |
| | Others | Antibiotic Cephalexin sodium | 4.5 |
| | | Carbenoxolone sodium | 4.7 |
| | | Chlorambucil sodium | 5.8 |
| OH | Enolic acid (Oxicam) derivatives | Piroxicam | 4.8 |
| | | Meloxicam | 4.5 |
| | | Lornoxicam | 1.8 |
| | | Warfarin sodium | 5.0 |
| PO$_4$ | Glucocorticoids (GCs) | Hydrocortisone sodium phosphate | 1.18 |
| | | Betamethasone sodium phosphate | 1.18 |
| | | Dexamethasone sodium phosphate | 1.89 |
| | | Dexamethasone hemisuccinate | 4.29 |
| COOH, OH | | Salsalate (Disalcid) | 3.4 |

The present invention further provides a method for preparing the pharmaceutical composition disclosed herein, comprising the steps of:
  (i) preparing a lipid solution using at least one vesicle-forming lipid;
  (ii) mixing the lipid solution from step (i) with a bicarbonate salt to form at least one liposome comprising a lipid bilayer and an internal aqueous medium, wherein the liposome is suspended in an external medium;
  (iii) adjusting the concentration of the bicarbonate salt in the external medium to produce a lower pH in the external medium of the liposome and a higher pH in the internal aqueous medium of the liposome, wherein the pH of the external medium is above the pK$_a$ of a weak acid drug; and
  (iv) adding the weak acid drug to the external medium.

In some embodiments, step (i) of the method comprises dissolving at least one vesicle-forming lipid in an organic solvent to form a lipid solution. The vesicle-forming lipid may be a mixture of a first phospholipid and a second phospholipid or a mixture of a first phospholipid and a charged lipid. In Step (ii), the lipid solution is then mixed with an aqueous buffer solution of a bicarbonate salt of a metal to form a suspension which comprises an external medium and at least one liposome, wherein the liposome is suspended in the external medium. In Step (iii), the concentration of the bicarbonate salt in the external medium is adjusted by replacing the external medium with another buffer solution lacking bicarbonate salts to produce a lower outside/higher inside pH gradient between the external medium and the internal phase of the liposomes. In Step (iv), the weak acid drug is added to the external medium of the suspension and the resulting suspension is incubated under a predetermined condition to effect drug loading into the internal phase of the liposomes.

In some embodiments, the concentration of the bicarbonate salt in the internal aqueous medium is about 50 mM to less than about 1000 mM in Step (iii) of the method.

In some embodiments, the pH of the external medium is above the pKa of prostacyclin in step (iii) of the method. In other embodiments, the pH of the external medium is at least one unit lower than that of the internal aqueous medium.

In some embodiments, the molar ratio of the drug to bicarbonate salt in the internal aqueous medium is from about 0.1:1 to 1:1 in Step (iv) of the method.

Additionally, the present invention provides a method for utilizing freeze-dried or frozen liposomes disclosed herein to load a weak acid drug into the internal phase of the liposomes.

In some embodiments, the concentration of bicarbonate salt in in the internal aqueous medium of the liposome is 50 mM or above, 100 mM or above, 150 mM or above, 200 mM or above, 250 mM or above, 300 mM or above, 350 mM or above, 400 mM or above, 450 mM or above, 500 mM or above, 600 mM or above, 700 M or above, 800 mM or above and at most less than 1000 mM. In some embodiments, the concentration of bicarbonate salt in the aqueous buffer solution is from 50 mM to less than 1000 mM, from 50 mM to 800 mM, from 200 mM to less than 1000 mM, from 200 mM to 800 mM, or from 200 mM to 600 mM, from 250 mM to less than 1000 mM, from 250 mM to 800 mM, or from 250 mM to 600 mM, from 300 mM to 600 mM. In an exemplary embodiment, the bicarbonate salt concentration in the internal aqueous medium of the liposome can be measured by any method known or will be known in the art, or by the following steps: (a) separate the bicarbonate salt in the external medium from that of the internal aqueous medium by dialysis or size exclusion chromatography; (b) the liposome suspension without the bicarbonate salt in the external medium is dissolved by methanol and the concentration of the bicarbonate salt in the internal aqueous medium is determined by ion chromatography. In some embodiments, the external medium is substantially free of bicarbonate salt.

In an embodiment, the pharmaceutical compositions of the present invention has a drug encapsulation efficiency of at least 50%, at least 55%, at least 60%, at least 65%, at least 70%, at least 75%, at least 80%, at least 85% or at least 90%.

In another embodiment, the molar ratio of the drug to bicarbonate salt in the internal aqueous medium of the liposome (hereafter drug/salt molar ratio) is about 0.1: 1 to about 1:1. In an exemplary embodiments, the drug/salt ratio is from about 0.1:1 to 0.9:1, from about 0.1:1 to 0.8:1, from about 0.1:1 to 0.7:1, from about 0.1:1 to 0.6:1 or from about 0.1:1 to 0.5:1.

In yet another embodiment, the weak acid drug encapsulated in the internal phase of the liposomes is at a concentration from 1 mM to 800 mM or above. In some embodiments, the drug encapsulated in the internal phase of the liposomes is at a concentration of 5 mM or above, 10 mM or above, 20 mM or above, 40 mM or above, 50 mM or above, 80 mM or above, or 100 mM or above, and at most 800 mM.

According to the present invention, the pharmaceutical composition described herein has a higher drug encapsulation efficiency, an increased molar ratio of the weak acid drug to the bicarbonate salt from about 0.1 to about 1, and a high encapsulated drug concentration. Without being bound by any particular theory, it is believed that higher encapsulated drug or drug loading in the pharmaceutical composition described herein delivers more drugs to the site of action, prolongs the effect of the encapsulated drug and is more effective in reducing the symptoms or signs of the disease.

The pharmaceutical composition of the present invention with a high drug encapsulation efficiency or a high drug loading as described herein can be administered at a therapeutically effective amount for treating a respiratory disease to a subject in need thereof. Examples of respiratory disease include, but are not limited to, pulmonary hypertension, chronic obstructive pulmonary disease (COPD), asthma, cystic fibrosis, lower respiratory tract infection, bronchiectasis, bronchitis, bronchiolitis or croup. In an exemplary embodiment, the respiratory disease is pulmonary hypertension and the weak acid drug is prostacyclin or prostaglandin. In another exemplary embodiment, the respiratory disease is COPD and the weak acid drug is steroid or prostaglandin. In yet another exemplary embodiment, the respiratory disease is asthma and the weak acid drug is steroid. In yet another exemplary embodiment, the respiratory disease is lower respiratory tract infection and the weak acid drug is an antibiotic.

In general, the term "treating" as used herein refers to the application or administration of a pharmaceutical composition described herein including at least one weak acid drug to a subject afflicted with a respiratory disease, a symptom or conditions of the respiratory diseases, or a progression of the respiratory disease, with the purpose to cure, heal, alleviate, relieve, alter, remedy, ameliorate, improve, or affect the disease, the symptoms or conditions of the disease, the disabilities induced by the disease, or the progression of the disease. The term "therapeutically effective amount" used herein refers to the amount of the weak acid drug to confer a therapeutic effect in a subject. The therapeutically effective amount may change depending on various factors, such as administration route and frequency, body weight and age. Persons skilled in the art may determine the dosage in each case based on the disclosure herein, established methods, and their own experience.

In particular, the liposome composition comprising a weak acid drug as described herein is administered by inhalation, injecting parenterally, i.e., intraarterialy, intravenously, intraperitoneally, subcutaneously, intra-vitreally, intrathecally, intraarticularly, intramuscularly, within other human body cavities, or dispersing via aerosol. Aerosol administration methods include intranasal and pulmonary administration. In some embodiments, the liposome composition of the invention is administered intravenously or intraperitoneally by a bolus injection or infusion.

The present invention is further illustrated by the following examples, which are provided for the purpose of demonstration rather than limitation. Those of skill in the art should, in light of the present disclosure, appreciate that many changes can be made in the specific embodiments which are disclosed and still obtain a like or similar result without departing from the spirit and scope of the invention.

EXAMPLE 1: THE EFFECT OF DIFFERENT SALTS FOR DRUG LOADING

1. Materials and Methods 1.1 PGE 1 Liposome Preparation Using Sodium Acetate $(NaC_2H_3O_2)$ Liposome colloidal suspensions were prepared by ethanol injection technique. Briefly, 496.8 mg of hydrogenated soy phosphatidylcholine (HSPC), 154.65 mg of cholesterol and 42.15 mg of 1,2-distearoly-sn-glycero-3-phosphoethanolamine-N-[methoxy(polyethylene glycol)-2000] (DSPE-PEG2000) were dissolved in 2.86 ml of ethanol. The lipid solution in ethanol was injected into 17.4 ml of sodium acetate (200 mM or 400 mM) with vigorous stirring at 60° C. Liposomes were formed as soon as the lipid solution was in contact with sodium acetate. This was followed by extruding the liposome suspension through a 200 nm and a 100 nm polycarbonate membrane (six times, respectively). The liposome with about 100 nm was obtained and diafiltrated against a citrate buffer (pH 5.5) to form a higher inside/lower outside pH gradient between the external medium and the internal aqueous medium of the liposomes. The empty liposome suspension was then stored at 4° C. before drug loading process.

PGE1 (alprostadil) was added to the liposome suspension in the preceding paragraph at various drug/lipid molar ratios at room temperature (25° C.) for 20 min. The PGE1 loaded liposome suspension was stored at 4° C.

1.2 PGE 1 Liposome Preparation Using Sodium Bicarbonate $(NaHCO_3)$

The liposome suspension was prepared according to the method described in Section 1.1, except that sodium acetate (200 mM or 400 mM) was replaced by sodium bicarbonate (e.g. 200 mM, 400 mM or other concentrations).

1.3 Quantitative Determination of Drugs

The amount of the drug encapsulated into the liposome was quantified using Waters Alliance® HPLC system with a Photodiode Array (PDA) Detector. Briefly, an aliquot of 100 μL of each sample solution was directly injected into the HPLC system with a mixture of methanol and phosphate buffer (6.7 mM conc., pH 3.0) at volume ratio of 80:20 as the mobile phase at flow rate of 1.0 mL/min. Separation was performed in C18 Column (Phenomenex Prodigy 5U ODS-3 150×4.6 mm), and then post-reaction was carried out by mixed with IN of KOH at 65° C. The peak of the drug e.g. PGE1 was detected at 280 nm. The retention time was about 4.6 minutes.

1.4 Encapsulation Efficiency

Encapsulation efficiency (EE), i.e. the percentage of the drug encapsulated (or loaded) in the internal aqueous medium of the liposomes to the total amount of the drug present in the liposome suspension (i.e. drug in the external medium and drug loaded into the internal aqueous medium of the liposomes) was quantified as follows. Briefly, the liposome suspension was subjected to column chromatography. The free or non-associated drug (i.e. the drug in the external medium) and the liposomes containing the encapsulated drugs in the internal aqueous medium were separated from each other by eluting the liposome suspension through a G-25 column. The amount of the free drug was determined using Waters HPLC with PDA detection, and the amount of the encapsulated drug in the internal aqueous medium of the liposome, after destructing the liposomes with methanol (90% methanol and 10% liposome suspension), was also determined using the same method. The encapsulation efficiency was calculated using the following formula, $$EE\ (\%) = \left(\frac{L}{L+F}\right) \times 100,$$

where L is the amount of the encapsulated drug in the internal aqueous medium of the liposomes, and F is the amount of the free drug in the external medium.

(*In a specific condition, the trapped volume is 0.0314 mL per mL of liposome suspension while the liposome particle size is around 110 nm and the phospholipid concentration is 10 mM. The trapped volume can be calculated by a method known in the art (Xu et al., International Journal of Pharmaceutics (2012) 423(2), pp. 410-418.)

1.5 Mean Particle Size and Polydispersity Index (PdI)

The mean particle size of the liposomes was evaluated by dynamic light scattering. The polydispersity index (PdI), a value indicating the size distribution of the liposomes, was determined using the same evaluation technique as for mean particle, with a particle size analyzer (Beckman Coulter Delsa™ Nano C particle analyzer).

2. Results 2.1 Sodium Bicarbonate Offers a Higher Drug Encapsulation Efficiency

Table 2 shows the drug encapsulation efficiency (E.E.) and the drug to salt molar ratio of the liposome suspensions using sodium bicarbonate and sodium acetate as the loading salts.

TABLE 2

The effect of bicarbonate salt and acetate salt for drug loading

| Loading Salts | Formulation | Internal Salt concentration [mM] | Measured drug concentration (μg/mL) | E.E. (%) | Internal drug concentration (mM) | Molar ratio of internal drug to internal salt |
|---|---|---|---|---|---|---|
| Sodium Acetate | SA-200-1 | 200 | 34.5 | 93.9% | 2.91 | 0.015 |
| | SA-200-2 | 200 | 52.6 | 89.5% | 4.23 | 0.021 |
| | SA-200-3 | 200 | 209.8 | 85.6% | 16.13 | 0.081 |
| | SA-400-1 | 400 | 26.5 | 90.6% | 2.16 | 0.005 |
| | SA-400-2 | 400 | 55.5 | 90.1% | 4.49 | 0.011 |
| | SA-400-3 | 400 | 203.7 | 81.9% | 14.99 | 0.037 |
| | SA-400-4 | 400 | 435.4 | 66.6% | 26.05 | 0.065 |
| Sodium Bicarbonate | SB-200-1 | 200 | 31.9 | 97.9% | 2.81 | 0.014 |
| | SB-200-2 | 200 | 175.5 | 94.2% | 14.85 | 0.074 |
| | SB-200-3 | 200 | 642.7 | 95.1% | 54.91 | 0.275 |
| | SB-200-4 | 200 | 934 | 95.9% | 80.47 | 0.402 |
| | SB-200-5 | 200 | 1860.8 | 86.7% | 144.94 | 0.725 |
| | SB-200-6 | 200 | 2294 | 84.0% | 173.12 | 0.866 |
| | SB-400-1 | 400 | 18.7 | 97.3% | 1.63 | 0.004 |
| | SB-400-2 | 400 | 56.53 | 97.0% | 4.93 | 0.012 |
| | SB-400-3 | 400 | 294 | 96.0% | 25.36 | 0.063 |
| | SB-400-4 | 400 | 543 | 93.9% | 45.81 | 0.115 |
| | SB-400-5 | 400 | 1037.3 | 93.5% | 87.14 | 0.218 |
| | SB-400-6 | 400 | 1940.8 | 92.8% | 161.81 | 0.405 |
| | SB-400-7 | 400 | 2727 | 73.3% | 179.58 | 0.449 |
| | SB-400-8 | 400 | 2982.4 | 66.9% | 179.25 | 0.448 | a. The liposome composition includes 10 mM of phospholipid (HSPC:Chol:mPEG-DSPE = 3:1.91:0.072)
b. Internal drug concentration (mM) = [Drug [μg/mL] × EE %/molecular weight]/[trapped volume (mL)*]
*In the example, the trapped volume is 0.0314 mL per mL of liposome suspension while the particle size of liposome is around 110 nm and phospholipid concentration is 10 mM.

In addition, the internal drug concentration (mM) was calculated as follows.

Internal drug concentration $(mM)$ =

[Drug [μg/ml] × $EE$ %/molecular weight]/[trapped volume*]

The results in Table 2 indicate sodium bicarbonate increases the drug encapsulation efficiency of a weak acid drug and significantly increases the drug concentration within the internal aqueous medium of the liposomes, compared to sodium acetate. Specifically, the drug to bicarbonate salt molar ratio is less than 0.1:1 using sodium acetate as a loading agent and the molar ratio cannot increase any further by doubling the concentration of sodium acetate, whereas the drug to salt molar ratio is higher than 0.1:1 using sodium bicarbonate as a loading agent.

EXAMPLE 2: THE EFFECT OF HUMAN PHYSIOLOGICAL CONDITION ON THE PHARMACEUTICAL COMPOSITIONS USING BICARBONATE SALT FOR DRUG LOADING

Liposome suspensions using various concentrations of sodium bicarbonate for PGE1 loading were prepared according to section 1.1 of Example 1. The liposome suspensions were incubated at 25° C. and 37° C. for 20 minutes in an external buffer with osmolarity between 280-300 mOsm/Kg, to simulate human physiological condition.

TABLE 3

The effect of temperature on the pharmaceutical compositions with various concentrations of sodium bicarbonate

| Bicarbonate concentration (mM) | External buffer Buffer (mOsm/Kg) | Citrate (mM) | pH | pH at different incubation temperatures 25° C. | 37° C. |
|---|---|---|---|---|---|
| 600 | 280 | 10 | 5.43 | 5.42 | 5.43 |
| 800 | 280 | 10 | 5.42 | 5.38 | 5.53 |
| 1000 | 280 | 10 | 5.78 | 5.37 | 6.68 (leakage) |
| 1300 | 280 | 10 | 5.5 | 5.44 | 6.74 (leakage) |

Incubating formulations with a bicarbonate concentration of higher than about 1000 mM in human physiological condition (37° C. and 280-300mOsm/Kg) generated more $CO_2$ and lead to liposome leakage. The leaked liposomes released bicarbonate salt and the drug from the internal aqueous medium into the external medium and increased the pH of external medium to higher than 6.5.

EXAMPLE 3: THE EFFECT OF DIFFERENT BICARBONATE SALT CONCENTRATIONS ON DRUG LOADING

The liposomal suspension was prepared according to the method in section 1.1 of Example 1 and PGE1 was loaded with different concentrations of sodium bicarbonate (50 mM, 150 mM, 200 mM, 250 mM, 300 mM, 400 mM, 500 mM, 600 mM, and 800 mM).

Table 4 shows the effect of bicarbonate salt concentrations on drug loading.

TABLE 4

| Loading Salts | Internal Salt [mM] | [PGE1] (μg/mL) | E.E. (%) | Internal [PGE1] (mM) | Internal drug to internal salt Molar ratio |
|---|---|---|---|---|---|
| Sodium Bicarbonate | 50* | 226.4 | 93.8% | 19.08 | 0.382 |
| | 150* | 700.7 | 95.7% | 60.25 | 0.402 |
| | 200* | 934.0 | 95.9% | 80.47 | 0.402 |
| | 250* | 1446.4 | 92.3% | 119.94 | 0.480 |
| | 300* | 1756.9 | 92.7% | 146.32 | 0.488 |
| | 400* | 1940.8 | 92.8% | 161.81 | 0.405 |
| | 500** | 1463.9 | 96.0% | 252.52 | 0.505 |
| | 600* | 2578.3 | 93.1% | 215.66 | 0.359 |
| | 800* | 1614.9 | 90.2% | 130.87 | 0.164 |

*10 mM of phospholipid
**5 mM of phospholipid

The results suggest for a fixed amount of phospholipid, the drug encapsulation efficiency is above 90% and the drug to salt molar ratio is higher than 0.1:1 with 50 mM to 800 mM of bicarbonate salt. Bicarbonate salt concentration of 500 mM provided the highest drug encapsulation efficiency and drug to salt molar ratio.

EXAMPLE 4: THE LOADING OF DIFFERENT WEAK ACID DRUGS USING BICARBONATE SALT

A first (4-1) liposome suspension comprising HSPC, cholesterol and DSPE-mPEG2000 at a molar ratio of 3:2:0.075 was prepared according to the method in Example 1.

A second (4-2) liposome suspension comprising HSPC, cholesterol and DSPG at a molar ratio of 3:2:0.075 was prepared according to the method in Example 1.

A third (4-3) liposome suspension comprising DPPC, Cholesterol and DSPE-mPEG2000 at a molar ratio of 3:2:0.075 was prepared according to the method in Example 1.

A fourth (4-4) liposome suspension comprising DSPC, DPPC, Cholesterol and mPEG2000-DSPE at a molar ratio of 2.7:0.3:2:0.075 was prepared according to the method of Example 1.

A fifth (4-5) liposome suspension comprising HSPC, Cholesterol, mPEG2000-DSPE and stearylamine at a molar ratio of 3:2:0.075:0.025 was prepared according to the method of Example 1.

A sixth (4-6) liposome suspension comprising HSPC, DMPC, Cholesterol, and mPEG2000-DSPE at a molar ratio of 2.7:0.3:2:0.075 was prepared according to the method of Example 1.

200 mM to 400 mM of bicarbonate salt was used to load various weak acid drugs into the first, second and the third liposomal suspensions at 25° C. or 40° C. over 20 min. The loaded drug liposome suspensions were stored at 4° C.

Table 5 shows the bicarbonate salt is an effective loading agent for various weak acid drugs encapsulated in various liposomal formulations, with a high the drug encapsulation efficiency (higher than 80%) and drug to salt molar ratio greater than 0.1:1.

TABLE 5

The drug loading data of various weak acid drugs using bicarbonate salt as a loading agent.

| Weak Acid Drug | Internal Salt [mM] | Liposomal Formulation | Measured [drug] (μg/mL) | E.E. (%) | Internal [drug] (mM) | Internal drug to internal salt molar ratio |
|---|---|---|---|---|---|---|
| Treprostinil[b] | 400 | (4-2) | 1530.0 | 97.6% | 121.78 | 0.304 |
| Treprostinil[b] | 400 | (4-3) | 1560 | 90.4% | 115.01 | 0.288 |
| Treprostinil[b] | 400 | (4-5) | 1500 | 93.7% | 114.62 | 0.287 |
| Treprostinil[b] | 400 | (4-6) | 1550 | 94.5% | 119.45 | 0.299 |

TABLE 5-continued

The drug loading data of various weak acid drugs using bicarbonate salt as a loading agent.

| Weak Acid Drug | Internal Salt [mM] | Liposomal Formulation | Measured [drug] (µg/mL) | E.E. (%) | Internal [drug] (mM) | Internal drug to internal salt molar ratio |
|---|---|---|---|---|---|---|
| Treprostinil[b] | 250 | (4-4) | 980 | 97.4% | 77.84 | 0.311 |
| MRE-269[b] | 400 | (4-2) | 174.6 | 98.7% | 65.41 | 0.164 |
| Iloprost[b] | 400 | (4-2) | 395.9 | 97.4% | 170.34 | 0.426 |
| PGE1[a] | 400 | (4-1) | 1940.8 | 92.8% | 161.81 | 0.405 |
| Methylprednisolone Hemisuccinate (MPSS)[b] | 400 | (4-1) | 1132.2 | 85.9% | 65.27 | 0.163 |
| Piroxicam[b] | 400 | (4-1) | 944.7 | 84.5% | 76.72 | 0.192 |
| Meloxicam[b] | 400 | (4-1) | 1019.9 | 92.8% | 85.78 | 0.214 |
| Lornoxicam[b] | 400 | (4-1) | 1106.3 | 93.3% | 88.41 | 0.221 |
| Ketorolac[a] | 400 | (4-1) | 1192.7 | 91.2% | 135.71 | 0.339 |
| Ketorolac[a] | 200 | (4-1) | 766.8 | 91.0% | 87.06 | 0.435 |
| Warfarin[b] | 400 | (4-1) | 1036.0 | 87.3% | 93.42 | 0.234 |

[a]drug loading at 25° C.,
[b]drug loading at 40° C.

EXAMPLE 5: THE EFFECT OF THE PH OF THE EXTERNAL MEDIUM OF THE LIPOSOME SUSPENSION ON DRUG LOADING

A first (5-1) liposome suspension comprising HSPC, cholesterol and mPEG2000-DSPE at a molar ratio of 3:2:0.075 and a second (5-2) and a third (5-3) liposome suspensions comprising HSPC, Cholesterol and mPEG2000-DSPE at a molar ratio of 3:2:0.28 were prepared. Treprostinil was loaded into the liposome suspensions with 200 mM of bicarbonate.

The pH of the external medium of the first (5-1) liposome suspension is above the pKa of the drug (the pKa of treprostinil is 4.5) and the pH of the external medium of the second liposome suspension (5-2) and the third liposome suspension (5-3) are below the pKa of the drug.

Table 6 shows the pH of the external medium of the liposome suspension plays an important role in drug loading. Specifically, the drug encapsulation efficiency is significantly higher if the pH of the external medium of the liposome suspension is above the pKa of the drug compared to that of the liposome suspension that is below the pKa of the drug (90.6% vs 27.3% and 33.5%). Similarly the molar ratio of internal drug to salt is higher than 0.1:1 if the pH of the external medium of the liposome suspension is above the pKa of the drug compared to that of the liposome suspension that is below the pKa of the drug, which is less than 0.1:1.

TABLE 6

The effect of pH of the external medium of the liposome suspension on drug loading

| Formulation | External medium buffer/pH | Measured [drug] (µg/mL) | E.E. (%) | Internal [drug] (mM) | Molar ratio of internal drug to internal salt |
|---|---|---|---|---|---|
| 5-1 | 10 mM citrate buffer/pH 5.5 | 300.0 | 90.6% | 22.17 | 0.111 |
| 5-2 | 10% sucrose/ pH 2.3 | 315.9 | 27.3%* | 7.03 | 0.035 |
| 5-3 | 10% sucrose/ pH 3.61 | 353.1 | 33.5%* | 9.65 | 0.048 |

*some drug precipitation noted during drug loading

EXAMPLE 6: THE THERAPEUTIC EFFICACY OF PHARMACEUTICAL COMPOSITIONS WITH HIGH DRUG LOADING

An in vivo evaluation of the therapeutic efficacy of the pharmaceutical composition of Example 4 (the 4-2 liposome suspension encapsulated about 1.5 mg of treprostinil using 400 mM bicarbonate salt) on pulmonary hypertension was performed using 18 male Sprague Dawley rats, each weighing approximately 300-350 g.

To induce pulmonary hypertension, a pressure catheter was inserted into the pulmonary artery of each rat. One end of the catheter was exposed at the nape of the neck and connected to a pressure transducer. 24 Hours after the catheter insertion, the rats were transferred into a hypoxic chamber where the oxygen ($O_2$) level was reduced to 10% ($FiO_2$=0.1) by increasing the level of nitrogen ($N_2$). Once stable pulmonary hypertension was established, each rat was administered with a single dose of the three test articles: saline (N=6), free treprostinil at 6 µg/kg (N=6) or the pharmaceutical composition of Example 4 with treprostinil at 6 µg/kg (liposomal treprostinil, N=6). The test article was administered using a microsprayer at the trachea bifurcation of the rat. Following the test article administration, mean pulmonary arterial pressure (PAP) was measured at scheduled time points.

The results show the liposomal treprostinil is more effective in achieving a maximum reduction of mean PAP post injection compared to free treprostinil (40% mean PAP reduction in the liposomal treprostinil group vs. 20% mean PAP reduction in the free treprostinil group).

What is claimed is:

1. A method for treating a respiratory disease, comprising the steps of administering a pharmaceutical composition comprising liposomes, said liposomes comprising:
   (a) a lipid bilayer, comprising vesicle-forming lipid; and
   (b) an internal aqueous medium inside the lipid bilayer, comprising a bicarbonate salt and a weak acid drug with a pKa between about 1 to about 6,
      wherein the liposomes are suspended in an external medium, the concentration of the bicarbonate salt is about 50 mM to less than about 1000 mM, the pH of the external medium is above the pKa of the weak acid drug and the vesicle-forming lipid comprises a mixture of a first phospholipid and a second phospholipid or a mixture of a first phospholipid and a charged lipid, and
      wherein the encapsulation efficiency of the weak acid drug is at least about 50%.

2. The method of claim 1, wherein the molar ratio of the weak acid drug to the bicarbonate salt is from about 0.1:1 to about 1:1.

3. The method of claim 1, wherein the concentration of the bicarbonate salt is about 250 mM to about 800 mM.

4. The method of claim 1, wherein the encapsulation efficiency of the weak acid drug is at least 80%.

5. The method of claim 1, wherein the first phospholipid is phosphatidylcholine (PC), phosphatidylglycerol (PG), phosphatidylinositol (PI), phosphatidic acid (PA), phosphatidylethanolamine (PE), phosphatidylserine (PS) or any combination thereof, the second phospholipid is a PEG modified phospholipid, a positively charged or a negatively charged phospholipid, and the charged lipid is a positively charged or a negatively charged lipid.

6. The method of claim 5, wherein the first phospholipid is HSPC, DSPC, DPPC, DMPC or any combination thereof and the second phospholipid is DSPG, DPPG, DMPG, PEG-DSPE, or any combination thereof and charged lipid is stearylamine, 1,2-dioleoyl-3-trimethylammonium-propane (DOTAP), 3ß-[N-(N',N'-dimethylaminoethane)-carbamoyl]cholesterol (DC-Cholesterol), N⁴-Cholesteryl-Spermine (GL67), dimethyldioctadecylammonium (DDAB), 1,2-di-O-octadecenyl-3-trimethylammonium propane (DOTMA), ethylphosphocholine (ethyl PC) or any combination thereof.

7. The method of claim 1, wherein the vesicle-forming lipid further comprises a sterol that is cholesterol, cholesterol hexasuccinate, ergosterol, lanosterol, or any combination thereof.

8. The method of claim 7, wherein the first phospholipid is phosphatidylcholine (PC), phosphatidylglycerol (PG), phosphatidylinositol (PI), phosphatidic acid (PA), phosphatidylethanolamine (PE), phosphatidylserine (PS) or any combination thereof, the second phospholipid is a PEG modified phospholipid, a positively charged or a negatively charged phospholipid, and the charged lipid is a positively charged or a negatively charged lipid, and the mole percent of the first phospholipid: cholesterol: the second phospholipid or the charged lipid is 50-70:20-45:0.1-10.

9. The method of claim 7, wherein the first phospholipid is HSPC, DSPC, DPPC, DMPC or any combination thereof, the second phospholipid is DSPG, DPPG, DMPG, PEG-DSPE, or any combination thereof and the sterol is cholesterol.

10. The method of claim 9, wherein the mole percent of the first phospholipid: cholesterol: the second phospholipid is 50-70:20-45:0.1-10.

11. The method of claim 7, wherein the first phospholipid is HSPC, DSPC, DPPC, DMPC or any combination thereof, the charged lipid is stearylamine, 1,2-dioleoyl-3-trimethylammonium-propane (DOTAP), 3ß-[N-(N',N'-dimethylaminoethane)-carbamoyl]cholesterol (DC-Cholesterol), N⁴-Cholesteryl-Spermine (GL67), dimethyldioctadecylammonium (DDAB), 1,2-di-O-octadecenyl-3-trimethylammonium propane (DOTMA), ethylphosphocholine (ethyl PC) or any combination thereof, the sterol is cholesterol.

12. The method of claim 11 wherein the mole percent of the first phospholipid: cholesterol: the charged lipid is 50-70:20-45:0.1-10.

13. The method of claim 1, wherein the bicarbonate salt is potassium bicarbonate, sodium bicarbonate, calcium bicarbonate, magnesium bicarbonate, cesium bicarbonate, lithium bicarbonate, nickel bicarbonate, ferrous iron bicarbonate or any combination thereof.

14. The method of claim 1, wherein the weak acid drug is a prostaglandin, a steroid, a non-steroidal anti-inflammatory drug (NSAID), or an anticoagulant.

15. The method of claim 14, wherein said prostaglandin is Prostaglandin E1 (PGE1), Prostaglandin E2 (PGE2), Epoprostenol, Iloprost, Beraprost, MRE-269, prostacyclin, treprostinil or Ralinepag.

16. The method of claim 14, wherein said steroid is hydrocortisone, methylprednisolone, betamethasone or dexamethasone.

17. The method of claim 14, wherein said NSAID is Piroxicam, Meloxicam, Lornoxicam, ketorolac or diclofenac.

18. The method of claim 10, wherein said weak acid drug is Prostaglandin E1 (PGE1), Prostaglandin E2 (PGE2), Epoprostenol, Iloprost, Beraprost, MRE-269, prostacyclin, treprostinil, Ralinepag, hydrocortisone, methylprednisolone, betamethasone, dexamethasone, Piroxicam, Meloxicam, Lornoxicam, ketorolac, diclofenac or warfarin.

19. The method of claim 12, wherein said weak acid drug is Prostaglandin E1 (PGE1), Prostaglandin E2 (PGE2), Epoprostenol, Iloprost, Beraprost, MRE-269, prostacyclin, treprostinil, Ralinepag, hydrocortisone, methylprednisolone, betamethasone, dexamethasone, Piroxicam, Meloxicam, Lornoxicam, ketorolac, diclofenac or warfarin.

20. A method for treating a respiratory disease, comprising the steps of administering a pharmaceutical composition comprising liposomes, said liposomes comprising:
   (a) a lipid bilayer, comprising a mixture of a first phospholipid that is HSPC, DSPC, DPPC, DMPC or any combination thereof, a second phospholipid that is DSPG, DPPG, DMPG, PEG-DSPE, or any combination thereof and cholesterol or a first phospholipid, that is HSPC, DSPC, DPPC, DMPC or any combination thereof, a charged lipid that is stearylamine, 1,2-dioleoyl-3-trimethylammonium-propane (DOTAP), 3ß-[N-(N',N'-dimethylaminoethane)-carbamoyl]cholesterol (DC-Cholesterol), N⁴-Cholesteryl-Spermine (GL67), dimethyldioctadecylammonium (DDAB), 1,2-di-O-octadecenyl-3-trimethylammonium propane (DOTMA), ethylphosphocholine (ethyl PC) or any combination thereof and cholesterol; and
   (b) an internal aqueous medium inside the lipid bilayer, comprising 50 mM to 800 mM bicarbonate salt and a prostaglandin,
      wherein the liposomes are suspended in an external medium, the pH of the external medium is above the pKa of the prostaglandin, and the encapsulation efficiency is over 80%.

* * * * *